US008354503B2

(12) United States Patent
Hedges

(10) Patent No.: US 8,354,503 B2
(45) Date of Patent: Jan. 15, 2013

(54) METHOD FOR EXTRACTING HYDROPHOBIN FROM A SOLUTION

(75) Inventor: Nicholas David Hedges, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 279 days.

(21) Appl. No.: 12/636,157

(22) Filed: Dec. 11, 2009

(65) Prior Publication Data

US 2010/0151525 A1    Jun. 17, 2010

(30) Foreign Application Priority Data

Dec. 16, 2008    (EP) .................................... 08171868

(51) Int. Cl.
*C07K 1/14* (2006.01)
*A61K 38/00* (2006.01)

(52) U.S. Cl. ......... 530/361; 530/350; 424/493; 424/499

(58) Field of Classification Search ........................ None
See application file for complete search history.

(56) References Cited

U.S. PATENT DOCUMENTS

| | | | |
|---|---|---|---|
| 2,604,406 A | 7/1952 | Blihovde |
| 2,844,470 A | 7/1958 | Akerboom et al. |
| 2,937,093 A | 5/1960 | Gorman et al. |
| 2,970,017 A | 2/1961 | Melnick |
| 3,266,214 A | 8/1966 | Kramme |
| 3,346,387 A | 10/1967 | Moncrieff et al. |
| 3,914,441 A | 10/1975 | Finney et al. |
| 3,946,122 A | 3/1976 | Scharp |
| 4,066,794 A | 1/1978 | Schur |
| 4,146,652 A | 3/1979 | Kahn et al. |
| 4,305,964 A | 12/1981 | Moran et al. |
| 4,325,980 A | 4/1982 | Rek et al. |
| 4,425,369 A | 1/1984 | Sakamoto et al. |
| 4,542,035 A | 9/1985 | Huang et al. |
| 4,627,631 A | 12/1986 | Sherman |
| 4,627,983 A | 12/1986 | Scharf et al. |
| 4,629,628 A | 12/1986 | Negro |
| 4,668,519 A | 5/1987 | Dartey et al. |
| 4,869,915 A | 9/1989 | Inayoshi et al. |
| 4,874,627 A | 10/1989 | Greig et al. |
| 4,946,625 A | 8/1990 | O'Lenick |
| 4,954,440 A | 9/1990 | Johal et al. |
| 4,960,540 A | 10/1990 | Friel et al. |
| 5,084,295 A | 1/1992 | Whelan et al. |
| 5,104,674 A * | 4/1992 | Chen et al. ..................... 426/573 |
| 5,202,147 A | 4/1993 | Traska et al. |
| 5,208,028 A | 5/1993 | Clement et al. |
| 5,215,777 A | 6/1993 | Asher et al. |
| 5,336,514 A | 8/1994 | Jones et al. |
| 5,393,549 A | 2/1995 | Badertscher et al. |
| 5,397,592 A | 3/1995 | Vermaas et al. |
| 5,436,021 A | 7/1995 | Bodor et al. |
| 5,486,372 A | 1/1996 | Martin et al. |
| 5,536,514 A | 7/1996 | Bishay et al. |
| 5,620,732 A | 4/1997 | Clemmings et al. |
| 5,624,612 A | 4/1997 | Sewall et al. |
| 5,681,505 A | 10/1997 | Phillips et al. |
| 5,738,897 A | 4/1998 | Gidley |
| 5,770,248 A | 6/1998 | Liebfred et al. |
| 5,980,969 A | 11/1999 | Mordini et al. |
| 6,096,867 A | 8/2000 | Byass et al. |
| 6,187,365 B1 | 2/2001 | Vaghela et al. |
| 6,238,714 B1 | 5/2001 | Binder et al. |
| 6,284,303 B1 | 9/2001 | Rowe et al. |
| 6,497,913 B1 | 12/2002 | Gray et al. |
| 6,579,557 B1 | 6/2003 | Benjamins et al. |
| 6,685,977 B1 | 2/2004 | Asano et al. |
| 6,914,043 B1 | 7/2005 | Chapman et al. |
| 2001/0048962 A1 | 12/2001 | Fenn et al. |
| 2002/0085987 A1* | 7/2002 | Brown et al. .............. 424/70.11 |
| 2002/0155208 A1 | 10/2002 | Benjamins et al. |
| 2002/0182300 A1 | 12/2002 | Groh et al. |
| 2002/0197375 A1 | 12/2002 | Adolphi et al. |
| 2003/0087017 A1 | 5/2003 | Hanselmann et al. |
| 2003/0099751 A1 | 5/2003 | Aldred et al. |
| 2003/0134025 A1 | 7/2003 | Vaghela et al. |
| 2003/0148400 A1 | 8/2003 | Haikara et al. |
| 2003/0166960 A1 | 9/2003 | de Vocht et al. |
| 2003/0175407 A1 | 9/2003 | Kunst et al. |
| 2003/0190402 A1 | 10/2003 | McBride |
| 2004/0109930 A1 | 6/2004 | Hooft et al. |
| 2004/0185162 A1 | 9/2004 | Finnigan et al. |
| 2005/0037110 A1 | 2/2005 | Windhab et al. |

(Continued)

FOREIGN PATENT DOCUMENTS

CA              271999 A         6/1927

(Continued)

OTHER PUBLICATIONS

Askolin et al. (2001) Overproduction, purification, and characterization of the Trichoderma reesei hydrophobin HFBI, Askolin et al. (2001) Appl. Microl. Biotechnol., vol. 57, pp. 124-130.*
Talbot et al. (1996) MPG1 Encodes a Fungal Hydrophobin Involved in Surface Interactions during Infection-Related Development of Magnaporthe grisea, Plant Cell., vol. 8, No. 6, pp. 985-999.*
Martin et al. (2000) Sc3p hydrophobin organization in aqueous media and assembly onto surfaces as mediated by the associated polysaccharide schizophyllan, Biomacromol., vol. 1, No. 1, pp. 49-60.*
Linder et al. (2005) Hydrophobins: the protein-amphiphiles of filamentous fungi, FEMS Microbiol. Rev., vol. 29, No. 5, pp. 877-896.*
Chakraborty et al. (1972) Stabilization of Calcium Sensitive Plant Proteins by Kapa-Carrageenan, vol. 37, pp. 719-721.*
Reference (2012, updated), "Carbohydrates", pp. 1-29.*
Linder, Hydrophobins: the protein-amphiphiles of filamentous fungi, Microbiology Reviews, Jan. 21, 2005, vol. 29 No. 5, 877-896.
*, Research pushes the right buttons, mushroom are the new fat, University of Birmingham, Feb. 25, 2008, *, 1-2.

(Continued)

*Primary Examiner* — Manjunath Rao
*Assistant Examiner* — Samuel Liu
(74) *Attorney, Agent, or Firm* — Alan A. Bornstein

(57) ABSTRACT

Process for extracting hydrophobin from a solution wherein carrageenan is added to the solution and the pH of the solution is brought below 3.5, and the ionic strength of the solution is below 0.5.

11 Claims, No Drawings

U.S. PATENT DOCUMENTS

| | | | |
|---|---|---|---|
| 2005/0058058 A1 | 3/2005 | Cho et al. | |
| 2005/0123666 A1 | 6/2005 | Vaghela et al. | |
| 2005/0123668 A1 | 6/2005 | Kodali et al. | |
| 2005/0129810 A1 | 6/2005 | Lindner et al. | |
| 2005/0193744 A1 | 9/2005 | Cockings et al. | |
| 2006/0024417 A1 | 2/2006 | Berry et al. | |
| 2006/0024419 A1 | 2/2006 | Aldred et al. | |
| 2007/0014908 A1 | 1/2007 | Bramley et al. | |
| 2007/0071865 A1 | 3/2007 | Aldred et al. | |
| 2007/0071866 A1 | 3/2007 | Cox et al. | |
| 2007/0116848 A1 | 5/2007 | Aldred et al. | |
| 2007/0286936 A1 | 12/2007 | Bramley et al. | |
| 2007/0298490 A1* | 12/2007 | Sweigard et al. | 435/320.1 |
| 2008/0175972 A1 | 7/2008 | Cox | |
| 2008/0254180 A1 | 10/2008 | Windhab et al. | |
| 2008/0305237 A1 | 12/2008 | Beltman et al. | |
| 2009/0136433 A1 | 5/2009 | Subkowski et al. | |
| 2009/0142467 A1 | 6/2009 | Aldred et al. | |
| 2010/0303998 A1 | 12/2010 | Cox et al. | |

FOREIGN PATENT DOCUMENTS

| | | |
|---|---|---|
| CA | 1094866 | 10/2003 |
| CA | 1218557 | 11/2004 |
| DE | 29715519 | 11/1997 |
| DE | 102004038685 | 2/2006 |
| EP | 216270 | 4/1987 |
| EP | 0274348 | 7/1988 |
| EP | 0285198 | 10/1988 |
| EP | 0322952 A2 | 7/1989 |
| EP | 336817 | 10/1989 |
| EP | 0336817 | 10/1989 |
| EP | 0426211 | 5/1991 |
| EP | 0426211 A1 | 5/1991 |
| EP | 0469656 | 2/1992 |
| EP | 0521543 | 1/1993 |
| EP | 0477825 B1 | 12/1996 |
| EP | 775444 A1 | 5/1997 |
| EP | 777969 | 6/1997 |
| EP | 0777969 | 6/1997 |
| EP | 0930017 | 7/1999 |
| EP | 1061006 | 12/2000 |
| EP | 1074181 A1 | 2/2001 |
| EP | 0747301 | 8/2001 |
| EP | 0783254 B1 | 8/2001 |
| EP | 0919134 | 11/2001 |
| EP | 0771531 B1 | 9/2002 |
| EP | 0995685 | 4/2003 |
| EP | 1400486 | 3/2004 |
| EP | 1520484 | 4/2005 |
| EP | 1520485 | 4/2005 |
| EP | 1557092 | 7/2005 |
| EP | 1621084 | 2/2006 |
| EP | 1621084 A1 | 2/2006 |
| EP | 1623631 | 2/2006 |
| EP | 1626361 A1 | 2/2006 |
| EP | 1541034 A1 | 6/2006 |
| EP | 1849461 A1 * | 10/2007 |
| EP | 2052628 | 4/2009 |
| GB | 459583 | 1/1937 |
| JP | 530006491 | 7/1978 |
| JP | 61293348 | 12/1986 |
| JP | 03164156 | 7/1991 |
| JP | 3244348 A | 10/1991 |
| KR | 2004018844 | 3/2004 |
| WO | WO9013571 | 11/1990 |
| WO | WO9111109 | 8/1991 |
| WO | WO9222581 | 12/1992 |
| WO | WO9403617 | 2/1994 |
| WO | WO9412050 | 6/1994 |
| WO | WO9413154 | 6/1994 |
| WO | WO9523843 | 9/1995 |
| WO | WO9611586 | 4/1996 |
| WO | WO9621362 | 7/1996 |
| WO | WO9639878 | 12/1996 |
| WO | WO9641882 | 12/1996 |
| WO | WO9804148 | 2/1998 |
| WO | WO9804699 | 2/1998 |
| WO | WO9954725 | 10/1999 |
| WO | WO0022936 | 4/2000 |
| WO | WO0114521 | 3/2001 |
| WO | WO0135756 A1 | 5/2001 |
| WO | WO0157076 | 8/2001 |
| WO | WO0174864 | 10/2001 |
| WO | WO0184945 A1 | 11/2001 |
| WO | WO03015530 A1 | 2/2003 |
| WO | WO03051136 A1 | 6/2003 |
| WO | WO03053383 | 7/2003 |
| WO | WO03096821 | 11/2003 |
| WO | WO2005058055 | 6/2005 |
| WO | WO2005058067 A1 | 6/2005 |
| WO | WO2005102067 | 11/2005 |
| WO | WO2005113387 | 12/2005 |
| WO | WO2006010425 | 2/2006 |
| WO | WO2007087967 | 8/2007 |
| WO | WO2008031796 A1 | 3/2008 |
| WO | WO2008116733 | 10/2008 |
| WO | WO2009047657 A2 | 4/2009 |
| WO | WO2010067059 | 6/2010 |

OTHER PUBLICATIONS

Calonje, et al., Properties of a hydrophobin isolated from the mycoparasitic fungus verticillium fungicola, Can J Microbiol, Dec. 13, 2002, 48, 1030-1034.

Lumsdon, et al., Adsorption of hydrophobin proteins at hydrophobic & hydrophilic interfaces, Colloids & Surfaces, Sep. 1, 2005, 44, 172-178.

Wosten, et al., Interfacial self-assembly of a hydrophobin into an amphipathic protein membrane mediates fungal attachment to hydrophobic surfaces, EMBO Journal, Jan. 1, 1994, 13, 5848-5854.

De Vries, et al., Identification & characterization of a tri-partite hydrophobin from Claviceps fusiformis, Eur J Biochem, Mar. 2, 1999, 262, 377-385.

Swern, Baileys Industrial Oil and Fat Products, John Wiley & Sons, Jan. 1, 1979, 1, 369.

Cruse, Whipped Soup is Tasty, St. Petersberg Independant, May 26, 1970, ., B-4.

Hunter, et al., The role of particles in stabilising foams and emulsions, Advances in Colloid & Interface Science, Jan. 1, 2008, 137, 57-81.

Scholtmeijer, et al., Fungal hydrophobins in medical and technical applications, Appl Microbiol Biotechnol, May 19, 2001, 56, 1-8.

Arbuckle, Ice Cream, Avi Publishing, Jan. 1, 1972, 2nd Ed, 284.

Wosten, et al., Hydrophobins the fungal coat unravelled, Biophysica Acta, May 29, 2000, 1469, 79-86.

CP Kelco US Inc., Certificate of Analysis for Keltrol RD, CP Kelco, Apr. 17, 2007, *, 1.

Berolzheimer, Culinary Arts Institute Encyclopedic Cookbook, Culinart Arts Institute, Jan. 1, 1988, *, 648.

Talbot, Aerial Morphogenesis Enter the Chaplins, Current Biology, Sep. 16, 2003, 13, R696-R698.

Murray, Stabilization of bubbles and foams. Current Opinion in Colloid & Interface Science, Aug. 3, 2007, 12, 232-241.

Murray, et al., Foam stability proteins and nanoparticles, Current Opinion in Colloid & Interface Sc, Jan. 1, 2004, 9, 314-320.

Damodaran, Adsorbed layers formed from mixtures of proteins, Current Opinion to Colloid & Interface Science, Oct. 27, 2004, 9, 328-339.

Dictionary.com, Stabilizer, Dictionary.com, Jun. 14, 2010, *, 1.

Bay, La Cucina Italiana Italian Cuisine, Edizioni Piemme, Jan. 1, 2002, *, 1233.

Eleves, Teadora Gliga, Eleves, Jun. 8, 2007, *, 1.

Nakari-Setala, et al., Differential expression of the vegetative and spore-bound hydrophobins of Trichoderma reesei, Eur J. Biochem, May 26, 1997, 248, 415-423.

Tchuenbou-Magaia, et al., Hydrophobris stabilised air-filled emulsions for the food industry, Food Hydrocolloids, Mar. 16, 2009; 23, 1877-1885.

Kershaw, et al., Hydrophobins and Repellents Proteins with Fundamental Roles in Fungal Morphogenesis, Genetics & Biology, Jan. 1, 1998, 23, 18-33.

Goh, Application and Uses of Palm and Palm Kernel Oils, Malaysian Oil Science and Technology, Apr. 8, 2002, 11, 46-50.

CRC, Fennema's Food Chemistry, CRC Press, Jan. 1, 2008, 4th Ed., pp. 727-728, Taylor & Francis Group.

Kilcast, Sensory perception of creaminess & its relationship with food, Food Quality an Preference, Jun. 20, 2002, 13, 609-623, Elsevier.

De Vocht, et al., Structural Characterization of the Hydrophobin SC3, Biophysical Journal, Apr. 1, 1998, 74, 2059-2068. Biophysical Journal.

Hui, Encyclopedia of Food Science & Tehcnology, John Wiley & Sons, Jan. 1, 1992, 1, 204-210.

Bailey, et al., Process Technol effects of deletion & amplification of hydrophobins I & II in transformants of Trich reesel, Appl Microbiol Biotechnol, Jan. 31, 2002, 58, 721-727.

Collen, et al., A novel two-step extraction method w detergent polymer sys for primary recovery of the fusion protein endoglucanase I-hydro I, Biochimica et Biophysica Acta, Jan. 15, 2002, 1569, No. 1-3, 139-150.

Linder, et al., The hydrophobins HFBI & HFBII from Trichoderma reesei showing efficient interatctions w nonionic surfactants in aqueous two-phase sys, Biomacromolecules, Jul. 1, 2001, 2, No. 2, 511-517.

McGregor, et al., Antifoam effects on ultrafiltration, Biotechnology & Bioengineering, Jan. 1, 1988, 31, No. 4, 385-389.

Chaisalee, et al., Mechanism of Antifoam Behavior of Solutions of Nonionic Surfactants Above the Cloud Point, Journal of Surfactants & Detergents, Oct. 1, 2003, 6, No. 4, 345-351.

Holmes, et al., Evauluation of antifoams in the expression of recombinant FC fusion protein in shake flask cultures, Microbial Cell Factories, Oct. 10, 2006, 5, No. 1, P30.

Hung, et al., Cloud-point extraction of selected polycyclic aromatic hydrocarbons by nonionic surfactants, Separation & Purification Tech, Aug. 20, 2007, 57, 1-10.

Cox, et al., Exceptional Stability of food foams using class II hydrophobin HFBII, Food Hydrocolloids, Jan. 1, 2009, 23, 366-376.

Cox, et al., Surface Properties of Class II Hydrophobins from Trichoderma reesei & Influence on bubble stability, Langmuir, Jun. 20, 2007, 23, 7995-8002.

Wessels, Hydrophobins Proteins that Change the Nature of the Fungal Surface, Advances in Microbial Physiology, Jan. 1, 1997, 38, No. 38, 1-45.

Wosten, Hydrophobins Multipurpose Proteins, Annu Rev Microbiol, Jan. 1, 2001, 55, 625-646.

Askolin, et al., Overproduction purification and characterization of Trichoderma reesei hydrophobin HFBI, Appl Microbiol Biotechnol, Aug. 9, 2001, 57, 124-130.

McCabe, et al., Secretion of Cryparin a Fungal Hydrophobin, Applied & Environmental Microbiology, Dec. 1, 1999, 65, No. 12, 5431-5435.

Askolin, et al., Interaction & comparison of a Class I Hydrophobin from schizophyllum commune & Class II Hydro form trichoderma reesei, Biomacromolecules, Jan. 10, 2006, 7, 1295-1301.

Co-pending appln. Berry et al., U.S. Appl. No. 11/168,209, filed Jun. 27, 2005.

Co-pending appln. Aldred et al., U.S. Appl. No. 11/168,214, filed Jun. 27, 2005.

Co-pending appln. Aldred et al., U.S. Appl. No. 11/524,977, filed Sep. 21, 2006.

Co-pending appln. Aldred et al., U.S. Appl. No. 11/525,060, filed Sep. 21, 2006.

Co-pending appln. Cox et al., U.S. Appl. No. 11/524,675, filed Sep. 21, 2006.

Co-pending appln. Bramley et al., U.S. Appl. No. 11/639,851, filed Dec. 15, 2006.

Co-pending appln. Cox et al., U.S. Appl. No. 11/699,601, filed Jan. 30, 2007.

Co-pending appln. Cox et al., U.S. Appl. No. 11/699,602, filed Jan. 30, 2007.

Co-pending appln. Burmester et al., U.S. Appl. No. 12/002,684, filed Dec. 18, 2007.

Co-pending application for Cox, et al., U.S. Appl. No. 12/682,717, filed Apr. 12, 2010.

Co-pending application Aldred et al., U.S. Appl. No. 12/287,957, filed Oct. 15, 2008.

Co-pending appln. Cox et al., U.S. Appl. No. 12/578,752, filed Oct. 14, 2009.

Co-pending application for Aldred, et al., U.S. Appl. No. 12/788,395, filed May 27, 2010.

Co-pending appln. Watts et al., U.S. Appl. No. 12/788,419, filed May 27, 2010.

Co-pending appln. Cox et al., U.S. Appl. No. 12/532,667, filed Sep. 23, 2009.

Co-pending appln. Cox et al., U.S. Appl. No. 12/532,670, filed Sep. 23, 2009.

Co-pending appln. Cox et al., U.S. Appl. No. 12/780,294, filed May 14, 2010.

Co-pending appln. Cox et al., U.S. Appl. No. 12/780,323, filed May 14, 2010.

Co-pending application Aumaitre et al., U.S. Appl. No. 12/409,549, filed Mar. 24, 2009.

Dickinson, Dec. 2, 2010, Mixed biopolymers at interfaces: Competitive adsorption and multilayer structures, Food Hydrocolloids, 25, 1966-1983.

Fox, 1992, Analytical methods for Milk Proteins, Advanced Dairy Chemistry 1: Proteins, vol. 1, pp. 1, 6-7.

Graham et al., Jul. 3, 1979, Proteins at Liquid Interfaces, Journal of Colloid and Interface Science, 70, 415-426.

Miquelim et al., 2010, pH Influence on the stability of foams with protein-polysaccharide complexes at their interfaces, Food Hydrocolloids, 24, No. 4, 398-405.

Patino and Pilosof, 2011, Protein-polysaccharide interactions at fluid interfaces, Food Hydrocolloids, 25, 1925-1937.

Schmitt, Feb. 27, 2012, Declaration of Christophe Schmitt, Declaration of Christophe Schmitt, 1-4.

Wang et al., May 31, 2004, Protease a Stability of Beer Foam II, China Academic Journal Electronic Publishing House, 11-15.

Guinee et al., 2004, Salt in Cheese: Physical, Chemical and Biological Aspects, vol. 1, 3rd Ed., pp. 207-259.

Katzbauer et al., Properties and applications of xanthan gum, Polymer Degradation and Stability, Jun. 19, 1997, vol. 59, pp. 81-84, Elsevier.

Guar Gum, Guargum biz, Jun. 14, 2010, p. 1.

Penttila, et al., Molecular Biology of Trichoderma & Biotechnological Applicatons, Handbook of Fungal Biotech, Jan. 1, 2004, 2nd Ed, pp. 413-427.

Talbot, 7 Fungal Hydrophobins, Howard & Gow, Jan. 1, 2001, vol. 7, pp. 145-159.

Guner, et al., Production of yogurt ice cream at different acidity, Intl Journ of Food Sc & Tech, Jan. 1, 2007, vol. 42, pp. 948-952.

Minor, et al., Preparation and sensory perception of fat-free foams effect of matrix properties and level of aeration, Intl Journ of Food Sc & Tech, Jan. 1, 2009, vol. 44, 735-747.

Soukoulis, et al., Impact of the acidification process hydrocolloids & protein fortifiers on the physical & Sensory properties of frozen yogurt, Intl Journal of Dairy Tech, May 2, 2008, vol. 61, No. 2, pp. 170-177.

Whitcomb, et al., Rheology of Guar Solutions, Journal of Applied Polymer Sc, Jan. 1, 1980, vol. 25, pp. 2815-2827.

Cheer, et al., Effects of Sucrose on the Rheological Behavior of Wheat Starch Pastes, Journal of Applied Polymer Science, Jan. 1, 1983, vol. 28, pp. 1829-1836.

Hakanpaa, et al., Atomic Resolution Structure of the HFBII Hydrophobin a Self-assembling Amphiphile, Journal of Biological Chemistry, Jan. 2, 2004, vol. 279, No. 1, 534-539.

Kloek, et al., Effect of Bulk and Interfacial Rheological Properties on Bubble Dissolution, Journal of Colloid & Interface Sc. Feb. 2, 2001, vol. 237, pp. 158-166.

Quintas, et al., Rheology of superstaurated sucrose solutions, Journal of Food Engineering, Jan. 1, 2006, vol. 77, pp. 844-852.

Van Der Werf, Green coatings healthy foods and drug targeting, Leads in Life Science, Jan. 1, 2000, vol. 5, p. 1.

Grant, Grant & Hackh's Chemical Dictionary, McGraw-Hill, Jan. 1, 1987, 5th Ed, pp. 212.

Russo, et al., Surface activity of the phytotoxin cerato-ulmin, Natl Research Council of Canada, Jan. 1, 1982, vol. 60, pp. 1414-1422.

Search proteins matching the sequence pattern used for the hydrophobin definition in patent EP 1926 399 B1, Nestle Research Center, Oct. 16, 2009, pp. 1-3.
Takai, et al., Cerato-ulmin, a wilting toxin of ceratocystis ulmi: isolation & some properties of cerato-ulmin from the culture of C. ulmi, Phytopath, Jan. 1, 1978, vol. 91, pp. 129-146.
Wosten, et al., Interfacial self-assembly of a fungal hydrophobin to a hydrophobic rodlet layer, Plant Cell, Nov. 1, 1993, vol. 5, pp. 1567-1574.
Stringer, et al., Cerato-ulmin a toxin involved in dutch elm disease is a fungal hydrophobin, Plant Cell, Feb. 1, 1993, *, pp. 145-146.
Fats Oils Fatty Acids Triglycerides, Scientific Psychic, Jan. 1, 2005, pp. 1-4.
Marshall, Ice Cream, Springer, Jan. 1, 2003, 6th Ed, pp. 70-73.
Mathlouthi, et al., Rheological properties of sucrose solutions and suspensions, Sucrose Properties & Application, Jan. 1, 1995, pp. 126-154.
Wessels, et al., Fungal hydrophobins proteins that function at an interface, Trends in Plant Science, Jan. 1, 1996, vol. 1, No. 1, pp. 9-15
Sienkiewicz, Whey and Whey Utilization, Verlag Th Mann, Jan. 1, 1990, 2nd Ed, pp. 82-33.
Davis, et al., Application of foaming for the recovery of surfactin from B. subtilis ATCC 21332 cultures, Enzyme & Microbial Technology, Jan. 1, 2001, vol. 28, pp. 346-354.
Arbuckle, Ice Cream, Ice Cream 2nd Ed 1972 pp. 35 266 284-285, Jan. 1, 1972, 2nd Edition, pp. 35, 266, 284-285.
Dr. E. Kododziejcxzyk, Adsortion of different proteins to Teflon sheets: Experimental Results, Nestle Research Center, Nov. 16, 2009.
CRC, Fennema's Food Chemistry, CRC Press, Jan. 1, 2008, 4th Ed., pp. 727-728.
Kilcast et al., Sensory perception of creaminess and its relationship with food structure, Food Quality and Preference, Jun. 20, 2002, vol. 13, pp. 609-623.
De Vocht et al., Structural Characterization of the Hydrophobin SC3, as a Monomer and after Self-Assembly at Hydrophobic/Hydrophilic Interfaces, Biophysical Journal, Apr. 1998, vol. 74, pp. 2059-2068.
Arbuckle, Ice Cream, Ice Cream, 1972, 2nd, p. 31.
Fellows, Principles and Practice, Food processing technology, 2000, 2nd, pp. 83, 140, 429.
Arbuckle, Ice Cream, Ice Cream, 1972, 2nd Ed., p. 265, Avi Publishing Company.
Lambou et al., Whey Solids as Agricultural Foam Stabilizers, Jr. of Agr. and Food Chemistry, 1973, 21 No. 2, pp. 257-263.
Sanderson, Applications of Xanthan Gum, British Polymer Jr., 1981, vol. 13, pp. 71-75.
Temple, Biological Roles for cerato-Ulmin, a Hydrophobin secreted by the elm pathogens, Opthiostoma ulmi and O. novo-ulmi, Micological Society of America, 2000, vol. 92, pp. 1-9.
Co-Pending application Bott et al., U.S. Appl. No. 13/378,143, filed Dec. 14, 2011.
European Search Report, Application No. EP 08171868, dated May 18, 2009.
International Search Report, International Application No. PCT/EP2009/066258, mailed Mar. 4, 2010.
Written Opinion, International Application No. PCT/EP2009/066258.
Arbuckle, 1972, Ice Cream, Ice Cream, 2nd Edition, pp. 15, 18, 35, 61, 65.
Goh, 2002, Applications and Uses of Palm and Palm Kernel Oils, Malaysian Oil Science & Technology, vol. 11, pp. 46-50.
Kinderlerer, 1997, Chrysosporium species, potential spoilage organisms of chocolate, Journal of Applied Microhlology, vol. 83, pp. 771-778.
Linder et al., 2001, The Hydrophobins HFBI and HFBII from Trichoderma reesei Showtng Efficient Interactions with Nonionic Surfactants in Aqueous Two-Phase Systems, Biomacromolecules, vol. 2, No. 2, pp. 511-517.
Lumsdon et al., 2005, Adsorption of hydrophobin proteins at hydrophobic and hydrophilic interfaces, Colloids and Surfaces B. Biointerfaces, vol. 44, pp. 172-178.
Pardun, 1977, Soy Protein Preparations as Antispattering Agents for Margarine, Fette Seifen Anstrichmittel, vol. 79, No. 5, pp. 195-203 (Abstract Only).
Samsudin, May 26, 2010, Low-Fat Chocolate Spread Based on Palm Oil, Malasyian Palm Oil Board, pp. 27-30.
Scott et al., 1983, Influence of Temperature on the Measurement of Water Activity of Food and Salt Systems, Journal of Food Science, vol. 48, pp. 552-554.
Co-Pending application Aldred et al., U.S. Appl. No. 13/378,143, filed Feb. 10, 2012.
Co-Pending application Mitchell et al., U.S. Appl. No. 13/498,157, filed Mar. 26, 2012.
Co-Pending application Hedges et al., U.S. Appl. No. 12/636,157, filed Dec. 11, 2009.
Fox, et al., Jan. 1, 2004, Cheese: Physical, Chemical and Biological Aspects, Cheese Chemistry, Physics & Microbiology, 3rd, vol. 1, 207-223 9 (Best Available Copy).

* cited by examiner

METHOD FOR EXTRACTING HYDROPHOBIN FROM A SOLUTION

TECHNICAL FIELD OF THE INVENTION

The present invention relates to method for extracting hydrophobin from a solution. In particular it relates to a method for extracting hydrophobin in a fermentation process.

BACKGROUND TO THE INVENTION

Foaming is a common problem in aerobic, submerged fermentations. Foaming is caused by the sparging of gas into the fermentation medium for the purpose of providing oxygen for the growth of the aerobic organism being cultivated (e.g. bacteria, yeasts, fungi, algae, cell cultures). If the fermentation medium contains surface active components such as proteins, polysaccharides or fatty acids, then foam can be formed on the surface of the medium as the sparged gas bubbles disengage from the liquid. Foaming creates a number of problems including the undesirable stripping of product, nutrients, and cells into the foam, and can make process containment difficult. A known method for controlling foaming is to use antifoams, of which several types are commonly used: silicone-based (e.g. polydimethylsiloxanes), polyalkylene glycols (e.g. polypropylene glycol), fatty acids, polyesters and natural oils (e.g. linseed oil, soybean oil). Antifoams replace foam-forming components on bubble surfaces, resulting in destruction of the foam by bubble coalescence. Antifoams are added at the start of and/or during the fermentation.

When the fermentation product is intended for use in foods, personal products or medicine, it is highly desirable that the product is excreted by the producing organism into the fermentation medium (i.e. extra-cellular, rather than intra-cellular production). This avoids the need to disrupt the cells by physical or chemical means in order to release the product for recovery. By maintaining the cells intact, the cellular material can be easily separated from the product so that it is free of intracellular and genetic material which is usually regarded as an undesirable contaminant. This can be especially important when the producing organism has been genetically modified. However, extra-cellular production may intensify the degree of foaming in the fermenter, especially if the product facilitates foam formation or enhances foam stability, for example a biosurfactant or a hydrophobin. The use of antifoams presents a particular problem in the extra-cellular production of such foaming agents for two reasons: firstly the amount of antifoam required is increased because the foaming agent itself contributes to foaming in the fermenter. Secondly, it is not necessary to remove the antifoam from most fermentation products since it is present in low concentrations which do not affect the functionality of the product. However, when the fermentation product is a foaming agent, the antifoam must be substantially removed since the presence of antifoam in the product will impair its functionality.

Bailey et al, Appl. Microbiol. Biotechnol. 58 (2002) pp 721-727 disclose the production of hydrophobins HFB I and HFB II by the fermentation of transformants of *Trichoderma reesei*. An antifoam (Struktol J633) was used to prevent foaming and the hydrophobin was purified using aqueous two phase extraction. However separation methods such as aqueous two phase extraction or chromatographic processes are expensive and may require food-incompatible chemicals.

It has now been found that, rather than removing the antifoam from the solution it is possible to remove the hydrophobin.

TESTS AND DEFINITIONS

Hydrophobins

Hydrophobins can be obtained by culturing filamentous fungi such as hyphomycetes (e.g. *Trichoderma*), basidiomycetes and ascomycetes. Particularly preferred hosts are food grade organisms, such as Cryphonectria parasitica which secretes a hydrophobin termed cryparin (MacCabe and Van Alfen, 1999, App. Environ. Microbiol 65: 5431-5435). Similarly, surfactin can be obtained from *Bacillus subtilis* and glycolipids from e.g. *Pseudomanas aeruginosa, Rhodococcus erythropolis, Mycobacterium* species and *Torulopsis bombicola* (Desai and Banat, Microbiology and Molecular Biology Reviews, March. 1997, pp 47-64).

In EP 1 623 631 we have previously found that hydrophobins allow the production of aqueous foams with excellent stability to disproportionation and coalescence. Because hydrophobins are highly effective foaming agents, their presence in the fermentation medium presents a particular challenge for foam control.

Hydrophobins are a well-defined class of proteins (Wessels, 1997, Adv. Microb. Physio. 38: 1-45; Wosten, 2001, Annu Rev. Microbiol. 55: 625-646) capable of self-assembly at a hydrophobic/hydrophilic interface, and having a conserved sequence:

(SEQ ID NO. 1)
$$X_n\text{-}C\text{-}X_{5\text{-}9}\text{-}C\text{-}C\text{-}X_{11\text{-}39}\text{-}C\text{-}X_{8\text{-}23}\text{-}C\text{-}X_{5\text{-}9}\text{-}C\text{-}C\text{-}X_{6\text{-}18}\text{-}C\text{-}X_m$$

where X represents any amino acid, and n and m independently represent an integer. Typically, a hydrophobin has a length of up to 125 amino acids. The cysteine residues (C) in the conserved sequence are part of disulphide bridges. In the context of the present invention, the term hydrophobin has a wider meaning to include functionally equivalent proteins still displaying the characteristic of self-assembly at a hydrophobic-hydrophilic interface resulting in a protein film, such as proteins comprising the sequence:

(SEQ ID NO. 2)
$$X_n\text{-}C\text{-}X_{1\text{-}50}\text{-}C\text{-}X_{0\text{-}5}\text{-}C\text{-}X_{1\text{-}100}\text{-}C\text{-}X_{1\text{-}100}\text{-}C\text{-}X_{1\text{-}50}\text{-}C\text{-}X_{0\text{-}5}\text{-}C\text{-}X_{1\text{-}50}\text{-}C\text{-}X_m$$

or parts thereof still displaying the characteristic of self-assembly at a hydrophobic-hydrophilic interface resulting in a protein film. In accordance with the definition of the present invention, self-assembly can be detected by adsorbing the protein to Teflon and using Circular Dichroism to establish the presence of a secondary structure (in general, α-helix) (De Vocht et al., 1998, Biophys. J. 74: 2059-68).

The formation of a film can be established by incubating a Teflon sheet in the protein solution followed by at least three washes with water or buffer (Wosten et al., 1994, Embo. J. 13: 5848-54). The protein film can be visualised by any suitable method, such as labeling with a fluorescent marker or by the use of fluorescent antibodies, as is well established in the art. m and n typically have values ranging from 0 to 2000, but more usually m and n in total are less than 100 or 200. The definition of hydrophobin in the context of the present invention includes fusion proteins of a hydrophobin and another polypeptide as well as conjugates of hydrophobin and other molecules such as polysaccharides.

Hydrophobins identified to date are generally classed as either class I or class II. Both types have been identified in fungi as secreted proteins that self-assemble at hydrophobic interfaces into amphipathic films. Assemblages of class I hydrophobins are generally relatively insoluble whereas those of class II hydrophobins readily dissolve in a variety of solvents. Preferably the hydrophobin is soluble in water, by which is meant that it is at least 0.1% soluble in water, preferably at least 0.5%. By at least 0.1% soluble is meant that no hydrophobin precipitates when 0.1 g of hydrophobin in 99.9 mL of water is subjected to 30,000 g centrifugation for 30 minutes at 20° C.

Hydrophobin-like proteins (e.g."chaplins") have also been identified in filamentous bacteria, such as *Actinomycete* and *Streptomyces* sp. (WO01/74864; Talbot, 2003, Curr. Biol, 13: R696-R698). These bacterial proteins by contrast to fungal hydrophobins, may form only up to one disulphide bridge since they may have only two cysteine residues. Such proteins are an example of functional equivalents to hydrophobins having the consensus sequences shown in SEQ ID NOs. 1 and 2, and are within the scope of the present invention.

More than 34 genes coding for hydrophobins have been cloned, from over 16 fungal species (see for example WO96/41882 which gives the sequence of hydrophobins identified in *Agaricus bisporus*; and Wosten, 2001, Annu Rev. Microbiol. 55: 625-646). For the purpose of the invention hydrophobins possessing at least 80% identity at the amino acid level to a hydrophobin that naturally occurs are also embraced within the term "hydrophobins".

Antifoams

The term "antifoam" includes both antifoams which are usually added before foaming occurs and also those which are usually added once the foam has formed (sometimes known as defoamers). A definition of antifoams used in the present invention is found in "Foam and its mitigation in fermentation systems"—Beth Junker—Biotechnology Progress, 2007, 23, 768-784.

Fermentation Process

The fermentation to produce hydrophobin is carried out by culturing the host cell in a liquid fermentation medium within a bioreactor (e.g. an industrial fermenter). The composition of the medium (e.g. nutrients, carbon source etc.), temperature and pH are chosen to provide appropriate conditions for growth of the culture and/or production of the foaming agent. Air or oxygen-enriched air is normally sparged into the medium to provide oxygen for respiration of the culture.

The antifoam may be included in the initial medium composition and/or added as required through the period of the fermentation. Common practice is to employ a foam detection method, such as a conductivity probe, which automatically triggers addition of the antifoam. In the present invention, the antifoam is preferably present at a final concentration of from 0.1 to 20 g/L, more preferably from 1 to 10 g/L.

The fermenter temperature during step i), i.e. during fermentation, may be above or below the cloud point of the antifoam. Preferably the fermenter temperature is above the cloud point of the antifoam, since the antifoam is most effective at causing bubble coalescence and foam collapse above its cloud point. The fermenter temperature is generally chosen to achieve optimum conditions for growth of the host cells and/or production.

BRIEF DESCRIPTION OF THE INVENTION

It is the object of the invention to provide a process for extracting hydrophobin from a solution wherein carrageenan is added to the solution and the pH of the solution is brought below 3.5, preferably below 3.

In a first preferred embodiment of the invention, the solution is then filtered to produce a retentate and a filtrate, hydrophobin being recovered from the retentate. In a second preferred embodiment of the invention, the solution is submitted to a centrifugation step to produce a supernatant which is removed, leaving a remaining phase. Hydrophobin is then removed from the remaining phase.

Preferably, the process comprises the step of cultivating a host cell in a fermentation medium wherein the host cell extra-cellularly secretes hydrophobin; and the fermentation medium contains an antifoam. More preferably, the fermentation medium is aerated by sparging air or oxygen-enriched air into it.

Preferably the hydrophobin is HFBI or HFBII from *Trichoderma reesei*.

Preferably the host cell is a genetically-modified fungus, more preferably a yeast, most preferably *Saccharomyces cerevisiae*.

Preferably the ionic strength of the solution is below 0.5, preferably below 0.4, more preferably below 0.3, even more preferably below 0.2

Preferably, carrageenan is kappa or iota carrageenan, more preferably iota carrageenan, Preferably also the carrageenan/hydrophobin ratio (w/w) is between 1:10 and 10:1, preferably above 1:5, more preferably above 1:1.

DETAILED DESCRIPTION OF THE INVENTION

The present invention will be further described in the following examples wherein the hydrophobin is always HFB II.

Example 1

Comparative

Starting concentration 145.4 µg/cm$^3$ of hydrophobin in 4.5 cm$^3$ of a 25 mM citric acid solution. The solution was filtered leading to a concentration in filtrate of 67.9 µg/cm$^3$ in 9 cm$^3$.

There for 93% of the original hydrophobin filtered through.

Example 2

Comparative

Starting concentration 146.3 µg/cm$^3$ of hydrophobin in 4.5 cm$^3$ of a 25 mM sodium Citrate. The solution was filtered leading to a concentration in filtrate of 68.0 µg/cm$^3$ in 9 cm$^3$.

Therefore again 93% of the original hydrophobin filtered through.

Example 3

Invention

Starting concentration 145.9 µg/cm$^3$ of hydrophobin in 4.5 cm$^3$ of a 25 mM citric acid solution+1% kappa carrageenan sheared gel. The solution was filtered leading to a concentration in filtrate of 3.8 µg/cm$^3$ hydrophobin in 9 cm$^3$.

Therefore only 5% of the hydrophobin filtered through.

Then 9 cm$^3$ of 25 mM sodium citrate at pH 8 were passed through filter. The concentration in the filtrate was 40.9 µg/ml, therefore 56% of the original hydrophobin was recovered that way.

Example 4

Comparative

Starting concentration 145.9 μg/cm$^3$ of hydrophobin in 4.5 cm$^3$ of a 25 mM citric acid solution+1% kappa carrageenan sheared gel.

Then add 0.325 cm$^3$ NaOH (to go to pH 7.0) and filter Concentration in filtrate=75.6 μg/cm$^3$ in 9 cm$^3$ Here, 100% of the hydrophobin ended in the filtrate despite the use of carrageenan, showing the importance of pH.

Example 5

Invention

Starting concentration 145.9 μg/cm$^3$ of hydrophobin in 4.5 cm$^3$ of a 25 mM citric acid solution+1% kappa carrageenan sheared gel.

Then add solid NaCl to give a concentration of 0.5M NaCl and filter. The concentration in filtrate is 50.9 μg/cm$^3$ in 9 cm$^3$. So, about 70% of the original amount of hydrophobin filtered through despite the right pH and the use of 1% kappa carrageenan sheared gel Then 9 cm$^3$ of 25 mM sodium citrate at pH 8 passed through filter leading to a concentration in filtrate of 13.8 μg/cm$^3$. Therefore, only 19% of the hydrophobin was recovered that way, showing the influence of the ionic strength on the whole process. The higher the ionic strength, the lower the recovery, everything else being equal.

Example 6.a

Invention

Starting concentration 145.9 μg/cm$^3$ of hydrophobin in 4.5 cm$^3$ of a 25 mM citric acid solution+0.025% iota carrageenan.

The concentration in filtrate was 1.6 μg/cm$^3$ in 9 cm$^3$, only 2% of the original hydrophobin having passed through.

Then 9 cm$^3$ of 25 mM sodium citrate at pH 8 passed through filter, leading to a concentration in filtrate=29.5 μg/cm$^3$ Over 40% of the original hydrophobin was recovered.

Example 6.b

Invention

Starting concentration 145.9 μg/cm$^3$ of hydrophobin in 4.5 cm$^3$ of a 25 mM citric acid solution+0.025% kappa carrageenan.

The concentration in filtrate was 28.4 μg/cm$^3$ in 9 cm$^3$, 39% of the original hydrophobin having passed through.

This example shows that iota carrageenan performs better that kappa carrageenan when retaining hydrophobin

Example 7

Comparative

Starting concentration 145.9 μg/cm$^3$ of hydrophobin in 4.5 cm$^3$ of a 25 mM citric acid solution+1% sheared pectin.

The concentration in filtrate was 57.3 μg/cm$^3$ in 9 cm$^3$, representing 79% of the original hydrophobin, showing that pectin does not work.

Example 8

Comparative

Starting concentration 145.9 μg/cm$^3$ of hydrophobin in 4.5 cm$^3$ of a 25 mM citric acid and 1% N creamer 46.

The concentration in filtrate was 64.2 μg/cm$^3$ in 9 cm$^3$ representing 88% of the original hydrophobin, showing that hydrophobic starch does not work.

The invention claimed is:

1. Process for extracting hydrophobin from a solution comprising the steps of:
    a) adding carrageenan to the solution;
    b) adjusting the pH of the solution to below 3.5;
    c) filtering the solution to produce a retentate and a filtrate;
    d) recovering the hydrophobin from the retentate;
    e) centrifuging the solution to produce a supernatant which is removed, leaving a remaining phase; and
    f) removing the hydrophobin from the remaining phase;
    wherein the resulting hydrophobin is suitable for use in foods, personal care products and medicine.

2. Process according to claim 1 further comprising the step of cultivating a host cell in the solution including a fermentation medium wherein the host cell extra-cellularly secretes hydrophobin; and the fermentation medium contains an antifoam.

3. Process according to claim 2 wherein the host cell is a genetically-modified fungus.

4. Process according to claim 3 wherein the host cell is a yeast.

5. Process according to claim 4 wherein the host cell is *Saccharomyces cerevisiae*.

6. Process according to claim 1 wherein the hydrophobin is HFBI or HFBII from *Trichoderma reesei*.

7. Process according to claim 1 wherein the solution has an ionic strength below 0.5.

8. Process according to claim 1 wherein the carrageenan is kappa or iota carrageenan.

9. Process according to claim 8 wherein the carrageenan is iota carrageenan.

10. Process according to claim 1 wherein the carrageenan/hydrophobin ratio (w/w) is between 1:10 and 10:1.

11. Process according to claim 1 wherein the carrageenan is a shear gel.

* * * * *